US012042287B2

(12) United States Patent
Kumar

(10) Patent No.: US 12,042,287 B2
(45) Date of Patent: Jul. 23, 2024

(54) CATHETER SYSTEM TO FACILITATE BLOOD COLLECTION AND RELATED METHODS

(71) Applicant: Becton, Dickinson and Company, Franklin Lakes, NJ (US)

(72) Inventor: Jithendra Kumar, Woodlands (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 784 days.

(21) Appl. No.: 16/989,363

(22) Filed: Aug. 10, 2020

(65) Prior Publication Data

US 2021/0068731 A1     Mar. 11, 2021

Related U.S. Application Data

(60) Provisional application No. 62/898,409, filed on Sep. 10, 2019.

(51) Int. Cl.
*A61B 5/15* (2006.01)
*A61M 25/06* (2006.01)
(Continued)

(52) U.S. Cl.
CPC .. *A61B 5/150992* (2013.01); *A61B 5/150213* (2013.01); *A61B 5/15074* (2013.01);
(Continued)

(58) Field of Classification Search
CPC .. A61M 2039/0036; A61M 2039/1072; A61M 2039/0081; A61M 25/0606; A61M 25/0097; A61M 5/0693; A61M 39/045; A61M 2039/064; A61M 2039/0686; A61M 25/0637; A61M 2039/027;
(Continued)

(56) References Cited

U.S. PATENT DOCUMENTS 4,834,708 A * 5/1989 Pillari ............... A61M 25/0637
604/165.04
5,215,537 A * 6/1993 Lynn ................ A61M 39/045
215/249

(Continued)

FOREIGN PATENT DOCUMENTS

WO      2015/123689      8/2015

*Primary Examiner* — Daniel L Cerioni
*Assistant Examiner* — Andrew E Hoffpauir
(74) *Attorney, Agent, or Firm* — Kirton McConkie; Whitney Blair; Kevin Stinger

(57) ABSTRACT

A catheter system may include a catheter adapter, which may include a distal end, a proximal end, a lumen extending through the distal end and the proximal end, and a side port in fluid communication with the lumen. A catheter may extend distally from the catheter adapter. A septum may be disposed within the lumen. The septum may include a first slit generally aligned with a longitudinal axis of the catheter and a second slit offset from the longitudinal axis of the catheter. An introducer needle may be secured within a needle hub and may extend through the catheter and the first slit of the septum. A winged needle set may include: a body; a needle extending distally from the body and through the second slit of the septum; an extension tube extending from the body; and a blood collection device coupled to the extension tube.

16 Claims, 9 Drawing Sheets

(51) Int. Cl.
*A61M 39/00* (2006.01)
*A61M 39/10* (2006.01)
(52) U.S. Cl.
CPC ........ *A61M 25/0606* (2013.01); *A61M 39/10* (2013.01); *A61M 25/0693* (2013.01); *A61M 2039/0036* (2013.01); *A61M 2039/1072* (2013.01); *A61M 2039/1077* (2013.01)
(58) Field of Classification Search
CPC .............. A61M 25/0071; A61M 39/10; A61B 5/150351; A61B 17/12109; A61B 5/150732
See application file for complete search history.

(56) References Cited

U.S. PATENT DOCUMENTS

| | | | | |
|---|---|---|---|---|
| 7,691,093 | B2* | 4/2010 | Brimhall | A61M 25/0693 604/506 |
| 10,874,844 | B2* | 12/2020 | Weaver | A61M 1/3661 |
| 2001/0041871 | A1* | 11/2001 | Brimhall | A61M 25/0637 604/167.02 |
| 2004/0143226 | A1* | 7/2004 | Marsden | A61B 5/150671 604/272 |
| 2005/0080398 | A1* | 4/2005 | Markel | A61M 25/0014 264/165 |
| 2007/0093778 | A1* | 4/2007 | Cindrich | A61M 5/158 604/500 |
| 2010/0204553 | A1* | 8/2010 | Sonderegger | A61M 25/0693 604/167.03 |
| 2011/0202037 | A1* | 8/2011 | Bolger | A61M 25/0105 604/523 |
| 2013/0090610 | A1* | 4/2013 | Stout | A61M 39/0693 604/256 |
| 2013/0218082 | A1* | 8/2013 | Hyer | A61M 25/0097 604/256 |
| 2014/0350485 | A1* | 11/2014 | Sonderegger | B29C 45/1657 604/533 |
| 2017/0043126 | A1* | 2/2017 | Jones | A61M 39/045 |
| 2019/0022367 | A1 | 1/2019 | Burkholz et al. | |

* cited by examiner

CATHETER SYSTEM TO FACILITATE BLOOD COLLECTION AND RELATED METHODS

RELATED APPLICATIONS

This application claims the benefit of U.S. Provisional Patent Application No. 62/898,409, filed Sep. 10, 2019, and entitled CATHETER SYSTEM TO FACILITATE BLOOD COLLECTION AND RELATED METHODS which is incorporated herein in its entirety.

BACKGROUND

Intravenous catheters are commonly used for a variety of infusion therapies. For example, intravenous catheters may be used for infusing fluids, such as normal saline solution, various medicaments, and total parenteral nutrition, into a patient. Intravenous catheters may also be used for withdrawing blood from the patient.

Common types of intravenous catheter are peripheral IV catheters ("PIVCs"), peripherally inserted central catheters ("PICCs"), and midline catheters. Intravenous catheters may include "over-the needle" catheters, which may be mounted over a needle having a sharp distal tip. The sharp distal tip may be used to pierce skin and the vasculature of the patient. Insertion of the intravenous catheter into the vasculature may follow the piercing of the vasculature by the needle. The needle and the intravenous catheter are generally inserted at a shallow angle through the skin into the vasculature of the patient with a bevel of the needle facing up and away from the skin of the patient.

In order to verify proper placement of the introducer needle and/or the intravenous catheter in the vasculature, a user generally confirms that there is flashback of blood, which may be visible to the user. In some instances, the introducer needle may include a notch disposed towards a distal end of the introducer needle, and in response to the distal tip of the introducer needle being positioned within the vasculature, blood may flow proximally through a needle lumen, exit the needle lumen through the notch, and then travel proximally between an outer surface of the introducer needle and an inner surface of the intravenous catheter.

Accordingly, where the intravenous catheter is at least partially transparent, the user may visualize a small amount of blood "flashback" and thereby confirm placement of the intravenous catheter within the vasculature. Presence of a vasculature entrance indicator, such as blood flashback, may facilitate successful placement of intravenous catheters. Once placement of the introducer needle within the vasculature has been confirmed, the user may temporarily occlude flow in the vasculature and withdraw the introducer needle, leaving the intravenous catheter in place for future blood withdrawal and/or fluid infusion.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure generally relates to a catheter system to facilitate blood collection, as well as related devices and methods. In some embodiments, a catheter system may include a catheter adapter, which may include a distal end, a proximal end, a lumen extending through the distal end and the proximal end, and a side port in fluid communication with the lumen. In some embodiments, the catheter system may include a catheter secured within the catheter adapter and extending distally from the catheter adapter.

In some embodiments, the catheter system may include a septum disposed within the lumen of the catheter adapter. In some embodiments, the septum may include a first slit and/or a second slit generally parallel to the first slit. In some embodiments, the first slit may be generally aligned with a longitudinal axis of the catheter. In some embodiments, the second slit may be offset from the longitudinal axis of the catheter. In some embodiments, the proximal end of the catheter adapter may include a proximal opening. In some embodiments, the longitudinal axis of the catheter may be offset from a center of the proximal opening.

In some embodiments, the catheter system may include a needle hub and an introducer needle secured within the needle hub. In some embodiments, the introducer needle may be aligned with a longitudinal axis of the catheter. In some embodiments, the introducer needle may extend through the catheter and the first slit of the septum. In some embodiments, the septum may accommodate both blood collection and the introducer needle. In some embodiments, the septum may include a generally elliptical shape with a cut along a plane angled with respect to the longitudinal axis of the catheter. In some embodiments, the cut may form a first face at a distal end of the septum. In some embodiments, the distal end of the septum may include the first face and a second face. In some embodiments, the second face may be proximate the first face and/or generally perpendicular to the longitudinal axis of the catheter.

In some embodiments, the septum may include a tunnel extending along and/or through the first face. In some embodiments, the tunnel may extend from the side port towards the longitudinal axis of the catheter. In some embodiments, the catheter adapter may include a slot aligned with the second slit and extending from a proximal end of the catheter adapter.

In some embodiments, the catheter system may include a winged needle set, which may include one or more of the following: a body; a tab extending outwardly from the body; a needle extending distally from the body and through the second slit of the septum; and an extension tube extending from the body. In some embodiments, the tab may be disposed within the slot. In some embodiments, the winged needle set may include an adapter coupled to a proximal end of the extension tube. In some embodiments, the winged needle set may include a plug plugging a proximal end of the adapter. In some embodiments, the proximal end of the plug may be configured to couple to a blood collection device. In some embodiments, the plug may provide air venting of the winged needle set and catheter system. In some embodiments, a distal end of the needle of the winged needle set may be blunt or sharp.

In some embodiments, a method of collecting blood may include priming a portion of the catheter system to a prime stop point. In some embodiments, the prime stop point may be proximate the side port. In some embodiments, after priming the portion of the catheter system to the prime stop point, the catheter system may be inserted into vasculature of a patient. In some embodiments, after inserting the catheter system into vasculature of the patient, the needle hub and the introducer needle may be removed from the catheter system. In some embodiments, after removing the needle hub and the introducer needle from the catheter system, blood may be collected using the winged needle set. In some embodiments, after collecting blood using the winged needle set, the winged needle set may be removed from the catheter system. In some embodiments, when the winged needle set is removed from the catheter system, blood may be disposed within the lumen distal to the septum and proximate the prime stop point.

It is to be understood that both the foregoing general description and the following detailed description are examples and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

Figure 1A:
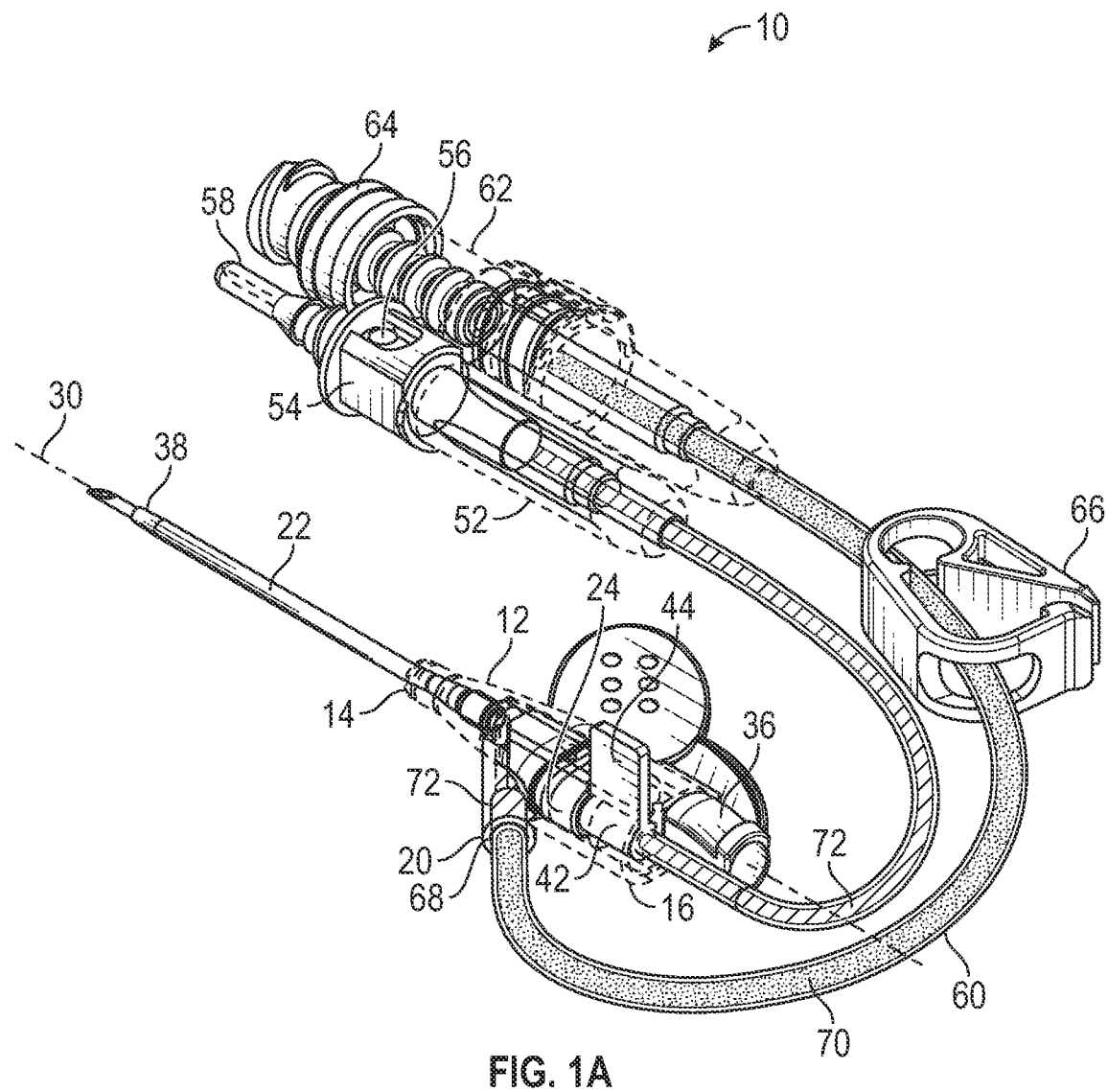
FIG. 1A is an upper perspective view of an example catheter system, according to some embodiments.
Figure 1B:
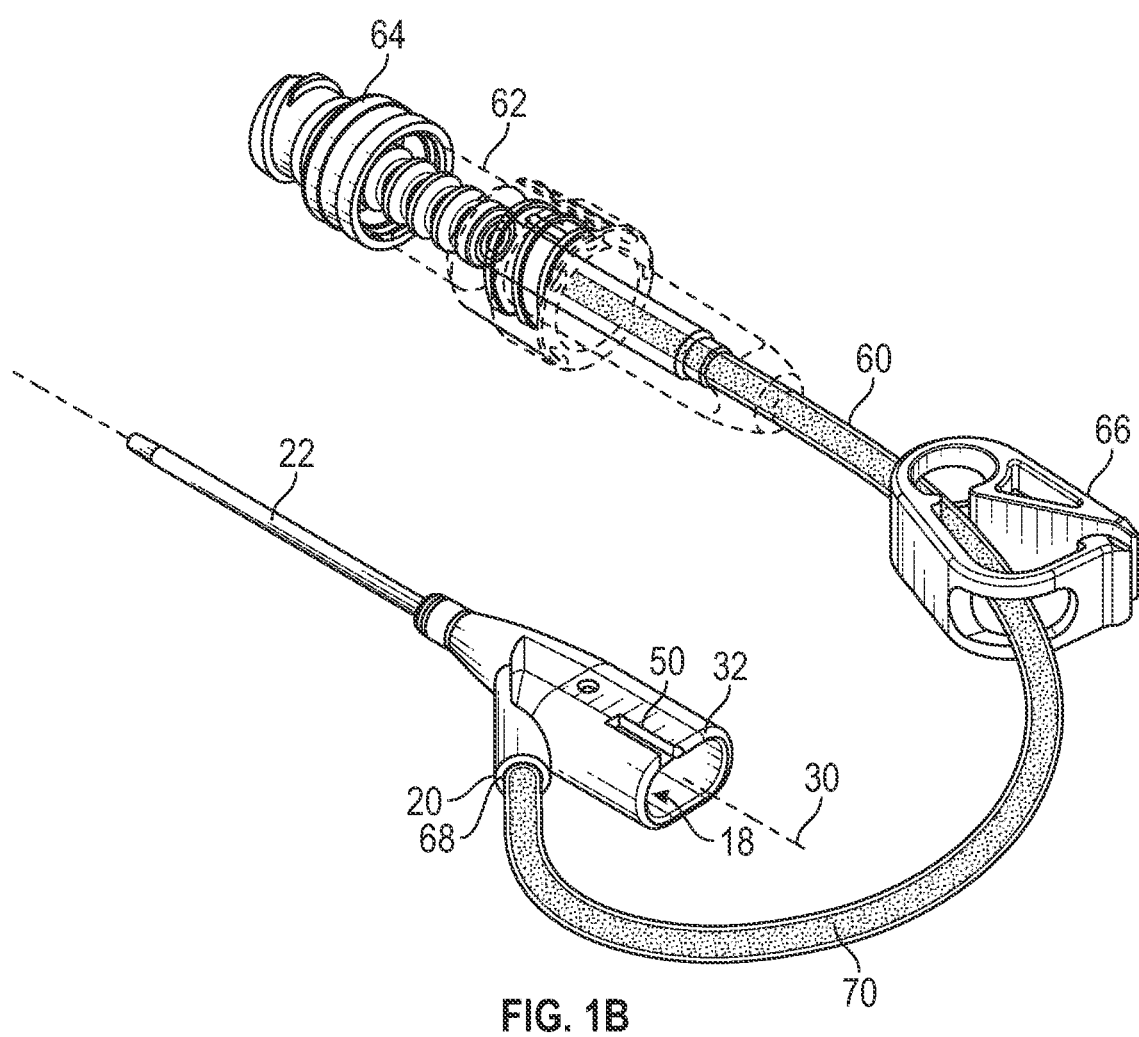
FIG. 1B is an upper perspective view of the catheter system 1A with an example needle assembly and an example winged needle set removed, according to some embodiments.
Figure 1C:
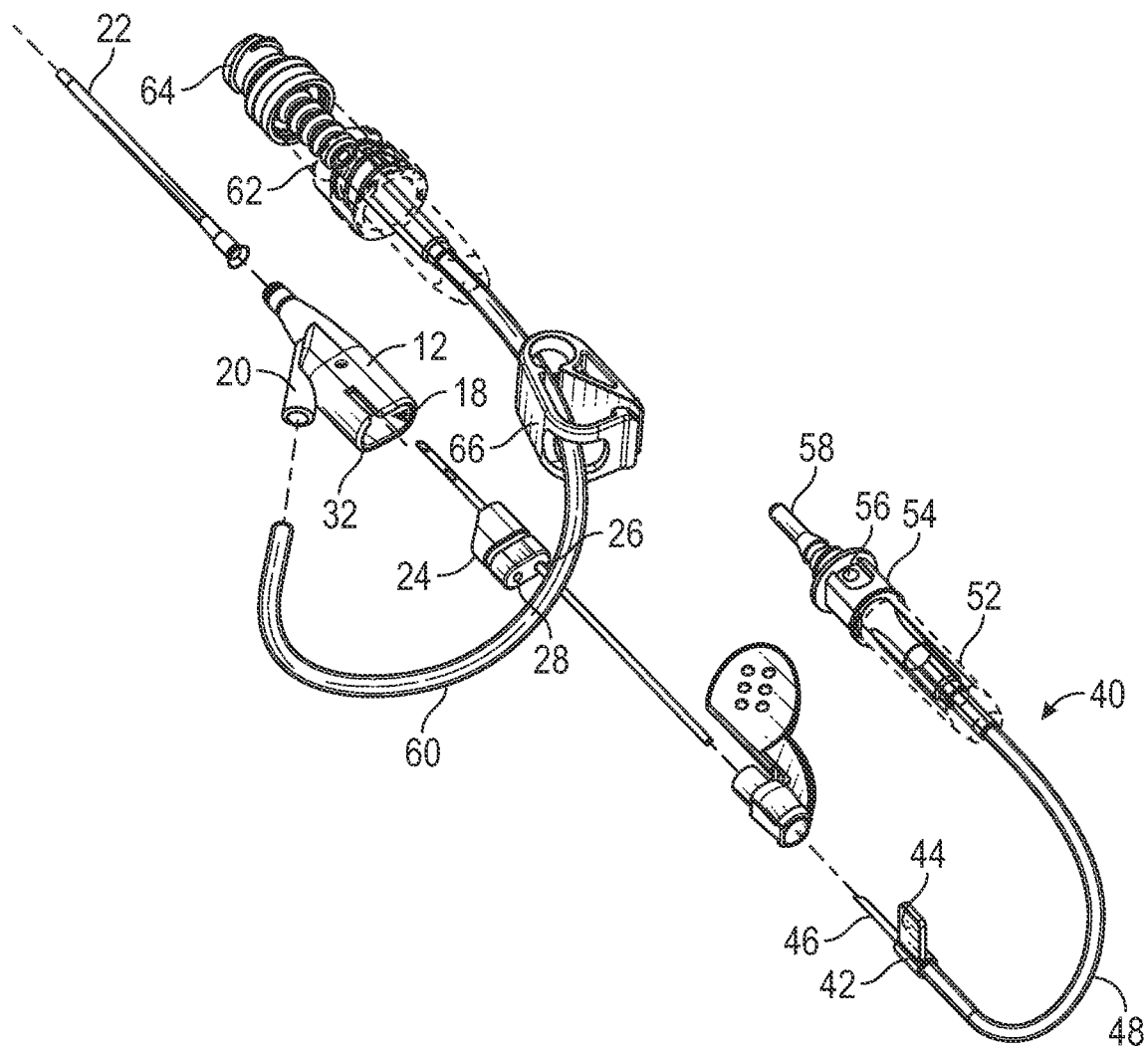
FIG. 1C is an exploded view of the catheter system of FIG. 1A, according to some embodiments.

Referring now to FIGS. 1A-1C, in some embodiments, a catheter system 10 may include a catheter adapter 12, which may include a distal end 14, a proximal end 16, a lumen 18 extending through the distal end 14 and the proximal end 16, and a side port 20 in fluid communication with the lumen 18. In some embodiments, the catheter system 10 may include a catheter 22 secured within the catheter adapter 12 and extending distally from the catheter adapter 12.

In some embodiments, the catheter system 10 may include a septum 24 disposed and secured within the lumen 18 of the catheter adapter 12. In some embodiments, the septum 24 may include a first slit 26 and/or a second slit 28, which may be generally parallel to the first slit 26. In some embodiments, the first slit 26 may be generally aligned with a longitudinal axis 30 of the catheter 22. In some embodiments, the second slit 28 may be offset from the longitudinal axis 30 of the catheter 22. In some embodiments, the proximal end 16 of the catheter adapter 12 may include a proximal opening 32. In some embodiments, the longitudinal axis 30 of the catheter 22 may be offset from a center of the proximal opening 32. In some embodiments, an outer surface of the catheter adapter 12 and/or the lumen 18 may include a generally elliptical shape.

In some embodiments, the catheter system 10 may include a needle assembly, which may include a needle hub 36 and an introducer needle 38 secured within the needle hub 36. In some embodiments, the introducer needle 38 may be aligned with the longitudinal axis 30 of the catheter 22. In some embodiments, the introducer needle 38 may extend through the catheter 22 and the first slit 26 of the septum 24. In some embodiments, the introducer needle 38 may extend distally beyond a distal end of the catheter 22. In some embodiments, the introducer needle 38 may include a sharp distal tip, which may be used to puncture vasculature of a patient.

In some embodiments, the catheter system 10 may include a winged needle set 40, which may include one or more of the following: a body 42; a tab 44 extending outwardly from the body 42; a needle 46 extending distally from the body 42 and through the second slit 28 of the septum 24; and an extension tube 48 extending from the body 42. In some embodiments, the catheter adapter 12 may include a slot 50 aligned with the second slit 28 and extending from the proximal end 16 of the catheter adapter 12. In some embodiments, the tab 44 may be disposed within the slot 50. In some embodiments, the slot 50 may help secure the tab 44 and the winged needle set 40 within the catheter adapter 12. In some embodiments, the tab 44 may facilitate removal of the winged needle set 40 from the catheter system 10 after blood is collected from the vasculature of the patient through the winged needle set 40.

In some embodiments, the winged needle set 40 may include an adapter 52, which may be coupled to a proximal end of the extension tube 48. In some embodiments, the proximal end of the extension tube 48 may be integrated into the adapter 52. In some embodiments, the adapter 52 may include a luer adapter, which may be straight, or another suitable adapter. In some embodiments, the winged needle set 40 may include a plug 54 plugging a proximal end of the adapter 52. In some embodiments, a proximal end of the plug 54 may be configured to couple to a blood collection device. In some embodiments, the plug 54 may include a BD VACUTAINER adapter. In some embodiments, the blood collection device may include a blood collection tube, a BD VACUTAINER tube or similar tube, which may include a hermetic seal at an open end and a vacuum.

In some embodiments, the proximal end of the plug 54 may include a cannula, which may extend in a proximal direction from the plug 54. In some embodiments, an elastomeric sheath 58 may be coupled to the plug 54, and a proximal end of the cannula may be enveloped within the elastomeric sheath 58. In some embodiments, the elastomeric sheath 58 may include an open distal end and a closed proximal end. In some embodiments, in response to the blood collection device pushing the elastomeric sheath 58 distally, the cannula may pierce the elastomeric sheath 58, and the cannula may insert into the blood collection device. In some embodiments, the plug 54 may include any suitable plug configured to couple to the blood collection device. In some embodiments, the adapter 52 may be coupled to the blood collection device via the plug 54.

In some embodiments, the plug 54 may provide air venting of the winged needle set 40 and the catheter system 10. In some embodiments, plug 54 may include a vent 56, which may include a porous membrane, microgroove, or any other suitable vent configured to pass air but not blood. In some embodiments, the vent 56 may be configured to provide continuous blood flashback due to air exiting the catheter system 10 at the vent 56.

In some embodiments, the introducer needle 38 may be constructed of metal or another suitable material. In some embodiments, the catheter 22 and/or the catheter adapter 12 may be constructed of constructed of polyisoprene, polyimide, latex, polyurethane, nylon, polyethylene, plastic, or another suitable material. In some embodiments, the septum 24 may be constructed of an elastomer. For example, the septum 24 may be constructed of silicon or another suitable material. In some embodiments, the septum 24 may be monolithically formed as a single unit.

In some embodiments, a distal end of an extension tube 60 may be integrated with the side port 20 of the catheter adapter 12. In some a proximal end of the extension tube 60 may be integrated with an adapter 62, which may include a luer adapter or another suitable adapter. In some embodiments, the adapter 62 may be coupled to a needleless connector 64 such as the BD SMARTSITE Needle-free Connector, the BD MAXZERO Needle-free Connector, or the BD Q-SYTE Needle-free Connector, for example. In some embodiments, a fluid infusion or priming device (such as, for example, a syringe) may be coupled to the needleless connector 64. In some embodiments, a pinch clamp 66 may be coupled to the extension tube 60 and configured to occlude or block fluid from flowing through the extension tube 60 in response to the pinch clamp 66 being in a clamped or closed position.

In some embodiments, a method of collecting blood may include priming a portion of the catheter system 10 to a prime stop point 68. In some embodiments, the prime stop point 68 may be proximate the side port 20. In some embodiments, the prime stop point 68 may be disposed outside the side port 20 and generally flush with an outer opening of the side port 20, such that the prime stop point 68 may be visible to a user.

In some embodiments, a priming device may be coupled to the needleless connector 64 and the catheter system 10 may be primed from the needleless connector 64 to the prime stop point 68. In some embodiments, in response to the catheter system 10 being primed from the needleless connector 64 to the prime stop point 68, the pinch clamp 66 may be moved to the closed position. In some embodiments, a priming solution 70 may include saline or another suitable material. In some embodiments, after priming the portion of the catheter system 10 to the prime stop point 68, the catheter system 10 may be inserted into vasculature of the patient. In particular, the catheter 22 and the introducer needle 38 may be inserted into the vasculature of the patient.

FIG. 1A illustrates the catheter system 10 after being primed to the prime stop point 68 and inserted into the vasculature of the patient, according to some embodiments. In some embodiments, the pinch clamp 66 may remain in the closed position during and/or after insertion of the catheter system 10 into the vasculature. In some embodiments, in response to inserting the catheter system 10 into the vasculature of the patient, blood 72 may flow through a notch in the introducer needle 38 or the catheter 22 into a space between the introducer needle 38 and the catheter 22. The blood 72 may then travel proximally into the lumen 18 distal to the septum 24. In some embodiments, the blood 72 may flow proximally to the prime stop point 68 and there may be some diffusion into the priming solution 70. In some embodiments, when the needle 46 of the winged needle set 40 extends through the septum 24, the blood 72 may flow through the winged needle set 40. In some embodiments, the blood 72 may correspond to blood flashback, indicating to the user presence of the catheter 22 within the vasculature.

In some embodiments, the needle assembly may be removed from the catheter system 10, which may facilitate more rapid blood collection through the catheter 22. In these embodiments, the blood 72 may flow through the catheter 22, which may not include the introducer needle 38 extending there through. In some embodiments, when the needle 46 of the winged needle set 40 extends through the septum 24, the blood 72 may flow through the winged needle set 40 and into the blood collection device.

As illustrated in FIG. 1B, for example, after inserting the catheter system 10 into vasculature of the patient, the needle hub 36 and the introducer needle 38 may be removed from the catheter system 10. In some embodiments, after removing the needle hub 36 and the introducer needle 38 from the catheter system 10, the blood 72 may be collected using the winged needle set 40. In some embodiments, after collecting the blood 72 using the winged needle set 40, the winged needle set 40 may be removed from the catheter system 10. In some embodiments, after collecting the blood 72 using the winged needle set 40, the winged needle set 40 may remain coupled to the catheter adapter 12, extending through the septum 34, for use in infusion. In some embodiments, when the winged needle set 40 is removed from the catheter system 10, blood may be disposed within the lumen 18 distal to the septum 24 and proximate the prime stop point 68.

Referring now to FIGS. 2A-2F, in some embodiments, the septum 24 may include a generally elliptical shape with a cut along a plane 74 angled with respect to the longitudinal axis 30 of the catheter 22. In some embodiments, the cut may form a first face 76 at a distal end 78 of the septum. In some embodiments, the distal end 78 of the septum 24 may include the first face 76 and a second face 80. In some embodiments, the second face 80 may be proximate the first face 76 and/or generally perpendicular to the longitudinal axis 30 of the catheter 22. In some embodiments, the first slit 26 and/or the second slit 28 may extend from a proximal end 82 of the septum 24. In some embodiments, the proximal end 82 may be generally oval-shaped.

In some embodiments, the septum 24 may include a groove or tunnel 84 extending along and/or through the first face 76. In some embodiments, the tunnel 84 may extend from the side port 20 towards the longitudinal axis 30 of the catheter. In some embodiments, the tunnel 84 may facilitate flow of fluid between the side port 20 and the lumen 18.

Figure 2A:
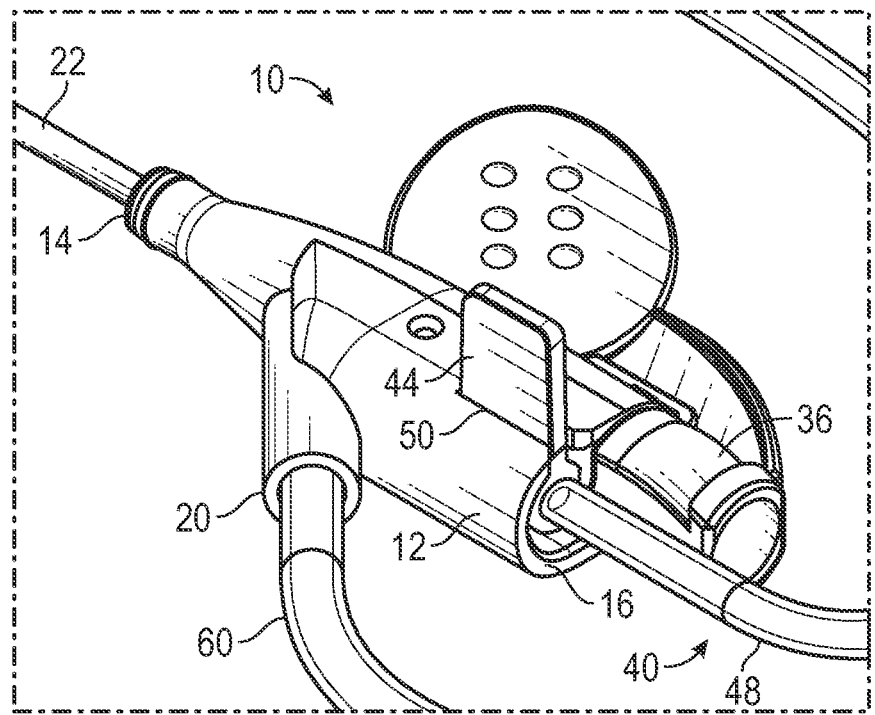
FIG. 2A is an enlarged upper perspective view of a portion of the catheter system of FIG. 1A, according to some embodiments.
Figure 2B:
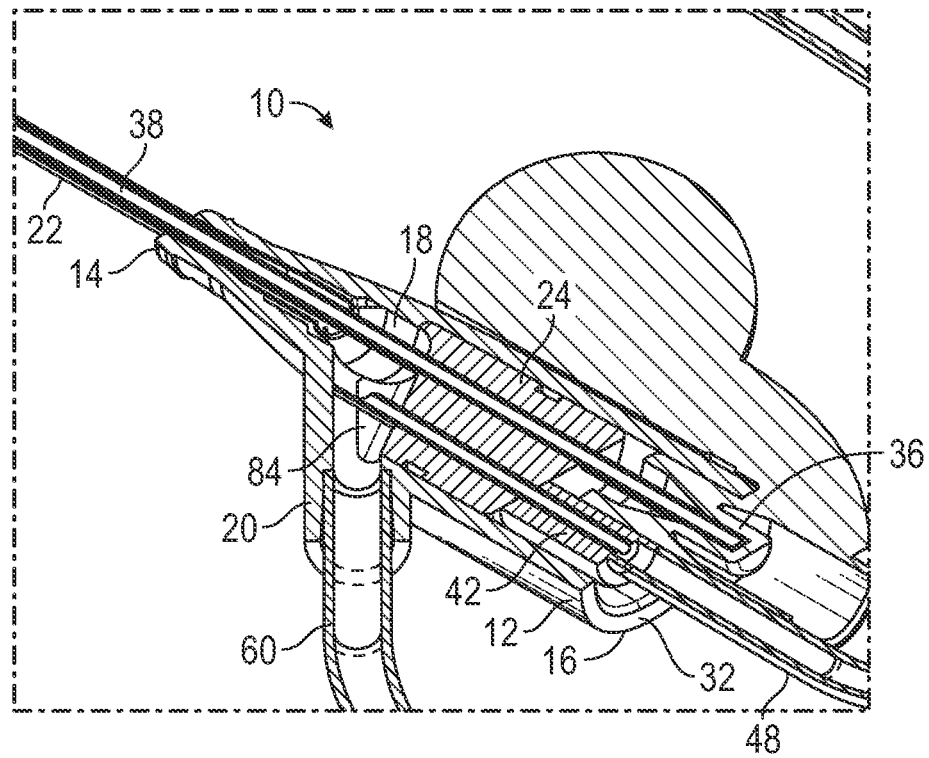
FIG. 2B is an enlarged cross-sectional view of the portion of FIG. 2A, according to some embodiments.
Figure 2C:
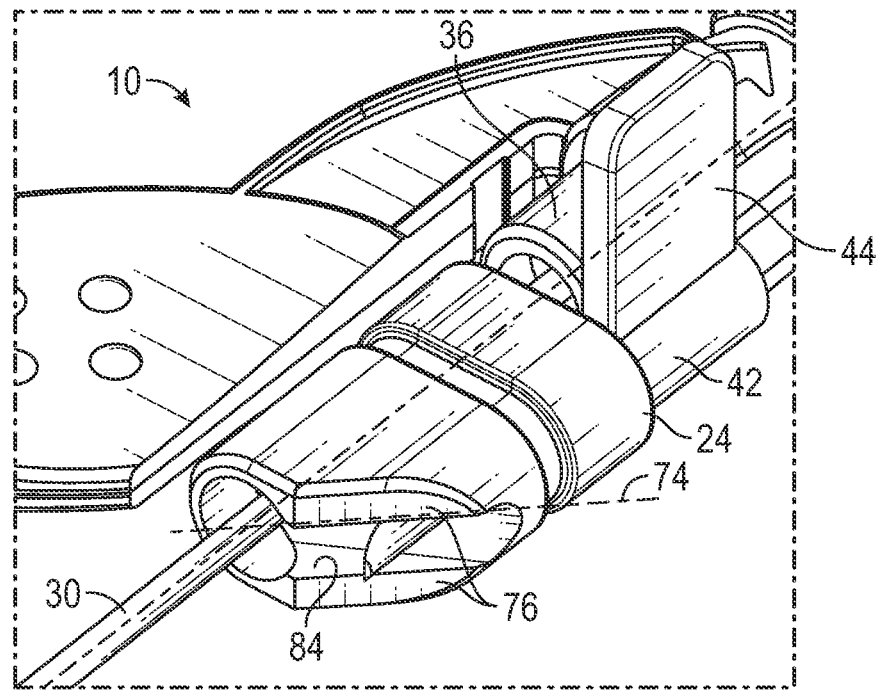
FIG. 2C is another enlarged upper perspective view of a portion of the catheter system of FIG. 1A, illustrating an example catheter adapter removed for illustration purposes, according to some embodiments.
Figure 2D:
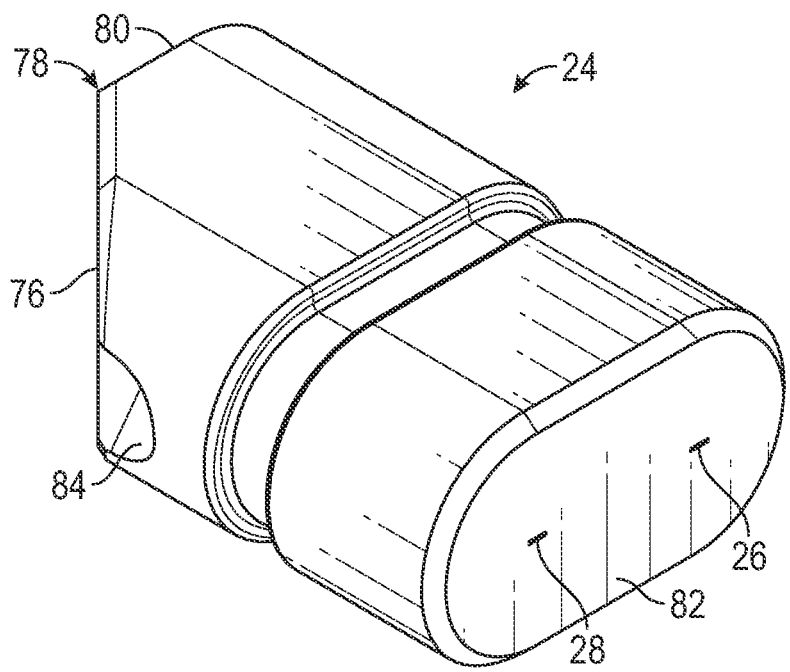
FIG. 2D is an upper perspective view of an example septum of the catheter system of FIG. 1A, according to some embodiments.
Figure 2E:
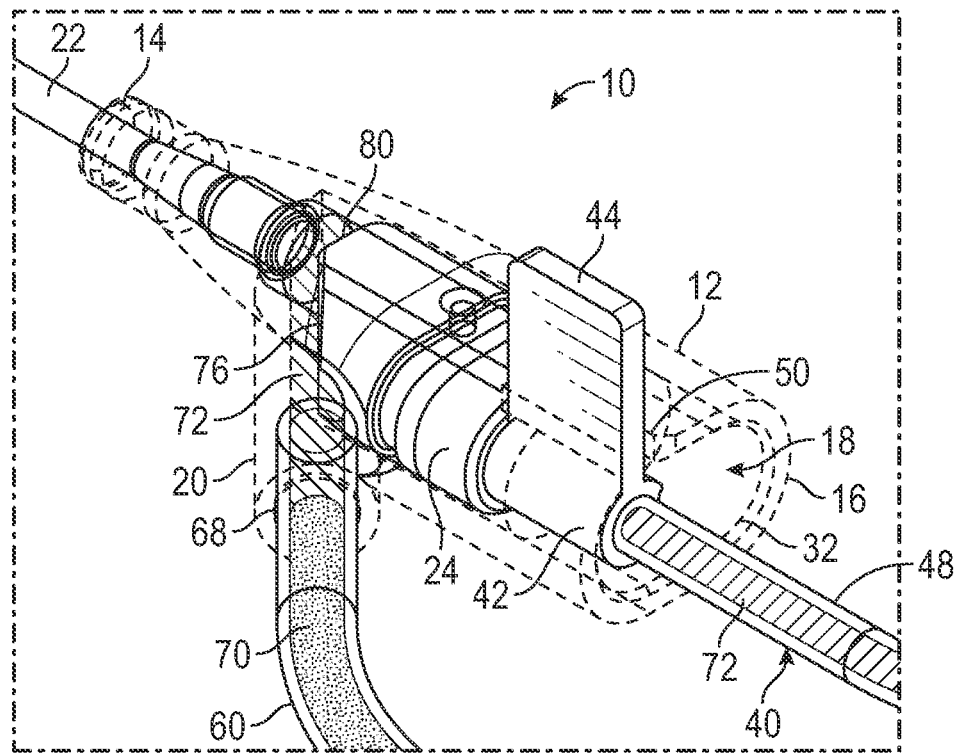
FIG. 2E is an upper perspective view of the catheter system of FIG. 1A, illustrating the needle assembly removed from the catheter system, according to some embodiments.
Figure 2F:
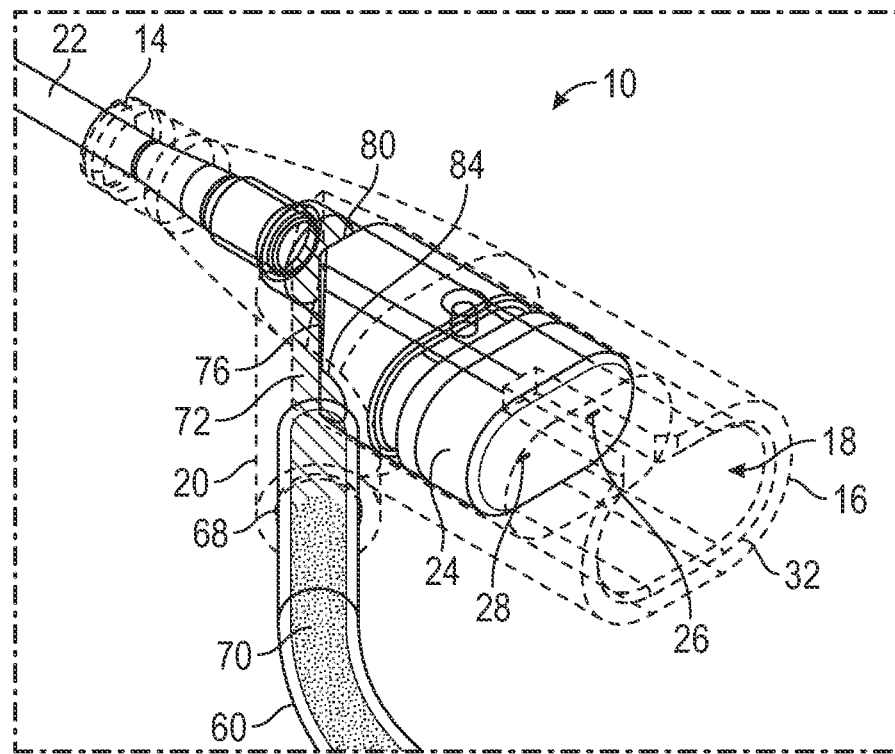
FIG. 2F is an upper perspective view of the catheter system of FIG. 1A, illustrating the needle assembly and the winged needle set removed from the catheter system after blood draw, according to some embodiments.

FIG. 2E illustrates the catheter system 10 after being primed to the prime stop point 68 and inserted into the vasculature of the patient, according to some embodiments. In some embodiments, as illustrated in FIG. 2F, after inserting the catheter system 10 into vasculature of the patient, the needle hub 36 and the introducer needle 38 may be removed from the catheter system 10. In some embodiments, when the winged needle set 40 is removed from the catheter system 10, the blood 72 may be disposed within the lumen 18 distal to the septum 24 and proximate the prime stop point 68.

Figure 3A:
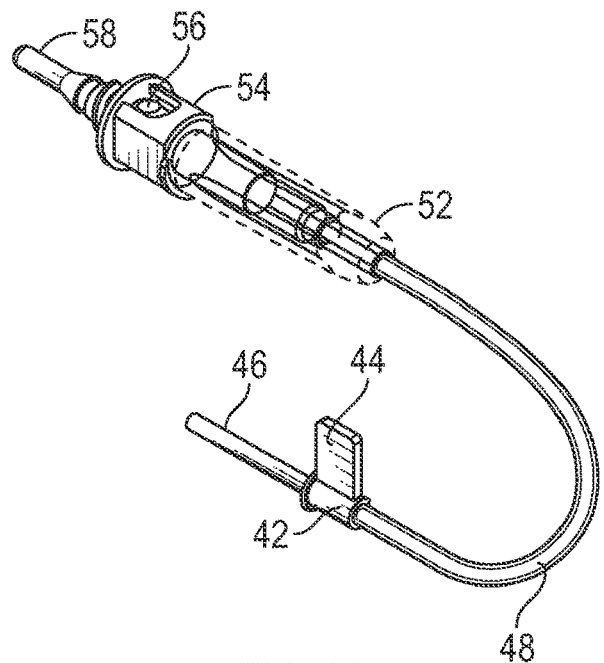
FIG. 3A is an upper perspective view of the winged needle set of the catheter system of FIG. 1A, according to some embodiments.
Figure 3B:
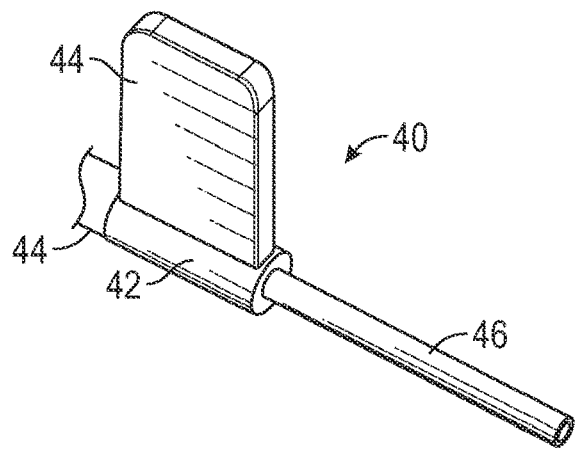
FIG. 3B is an upper perspective view of an example distal end of the winged needle set of the catheter system of FIG. 1A, according to some embodiments.
Figure 3C:
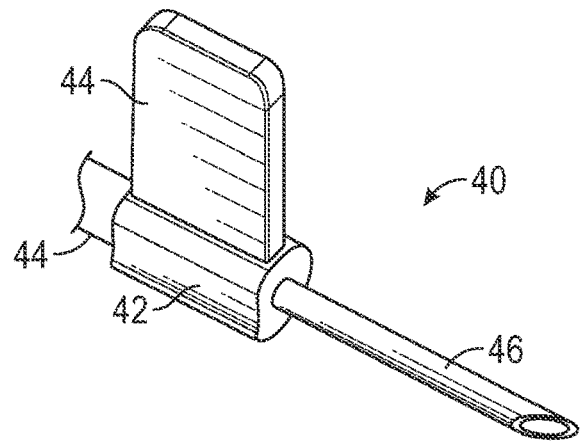
FIG. 3C is an upper perspective view of another example distal end of the winged needle set of the catheter system of FIG. 1A, according to some embodiments.

Referring now to FIGS. 3A-3C, the winged needle set 40 is illustrated, according to some embodiments. In some embodiments, a distal end of the needle 46 may be blunt (as illustrated, for example, in FIG. 3B) or sharp (as illustrated, for example, in FIG. 3C). In some embodiments, the catheter system 10 may provide the freedom to use a needle 46 that has a larger size or gauge than the introducer needle 38, which in some cases may be restricted to 24g or 26g, depending on the application. Thus, the needle 46 may facilitate a higher flow rate and/or reduction in hemolysis. In some embodiments, the catheter system 10 may be preassembled with the winged needle set 40 extending through the septum 24, which may reduce potential contamination and/or increase user-friendliness.

Figure 4A:
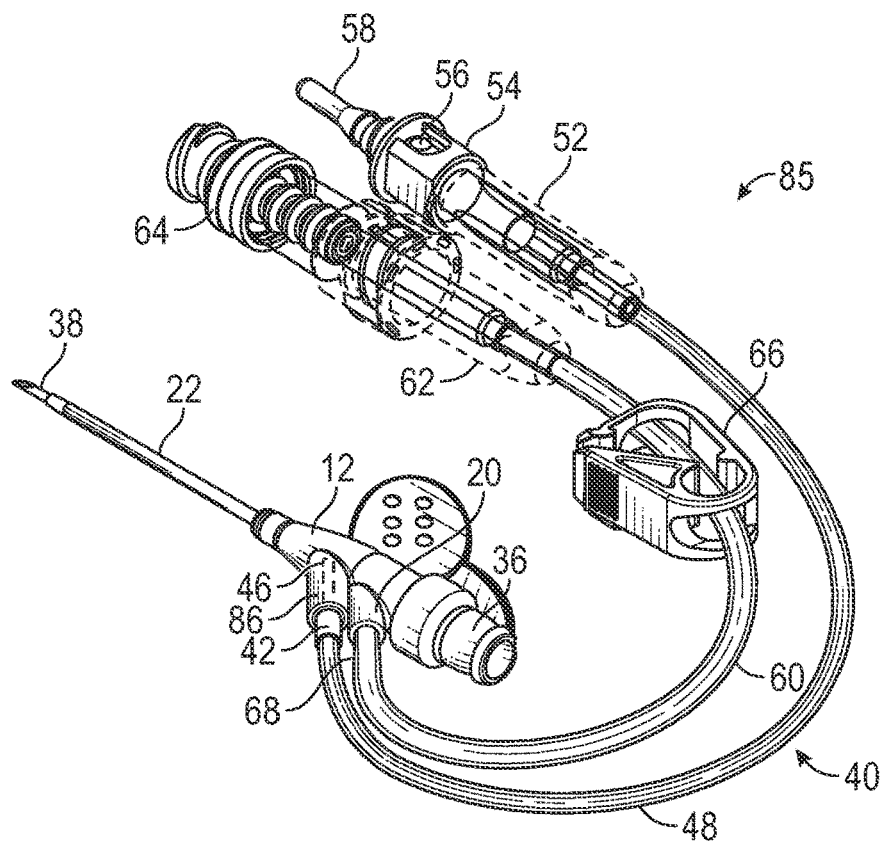
FIG. 4A is an upper perspective view of another catheter system, according to some embodiments.
Figure 4B:
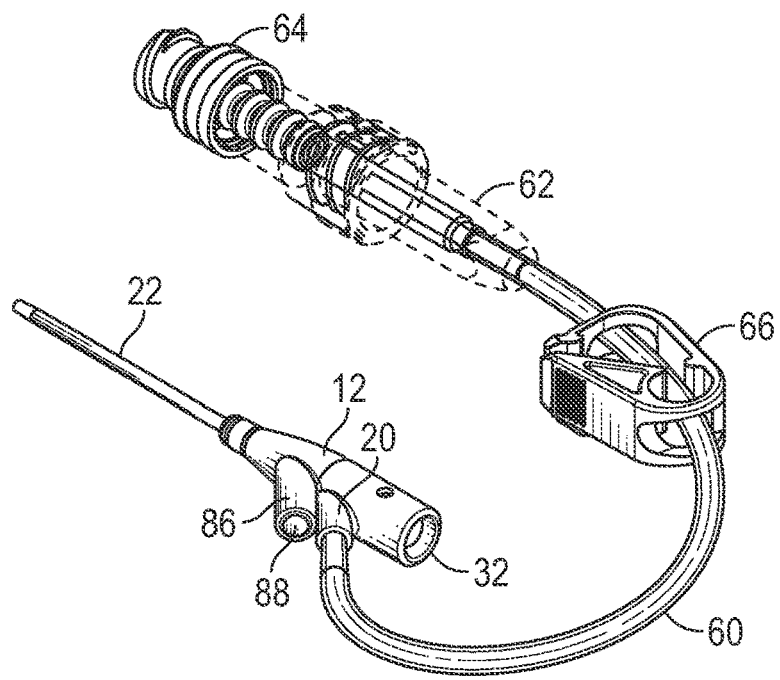
FIG. 4B is an upper perspective view of the catheter system of FIG. 4A, illustrating an example needle assembly and example winged needle set removed, according to some embodiments.

Referring now to FIGS. 4A-4B, another catheter system 85 is illustrated, according to some embodiments. In some embodiments, the catheter system 85 may be similar or identical to the catheter system 10 described with respect to FIGS. 1-3 in terms of one or more included components and/or operation. In some embodiments, the winged needle set 40 may be inserted into another side port 86, which may be in fluid communication with the lumen 18. In some embodiments, the other side port 86 through which the winged needle set 40 may be inserted may facilitate flushing of residual blood after blood collection. In some embodiments, a septum 88 disposed within the other side port 86 and/or the lumen 18 may be configured such that the winged needle set 40 inserts through the septum to communicate with the lumen 18. In some embodiments, the introducer needle 38 may be inserted through the septum 88 or another septum disposed within the lumen 18.

Figure 4C:
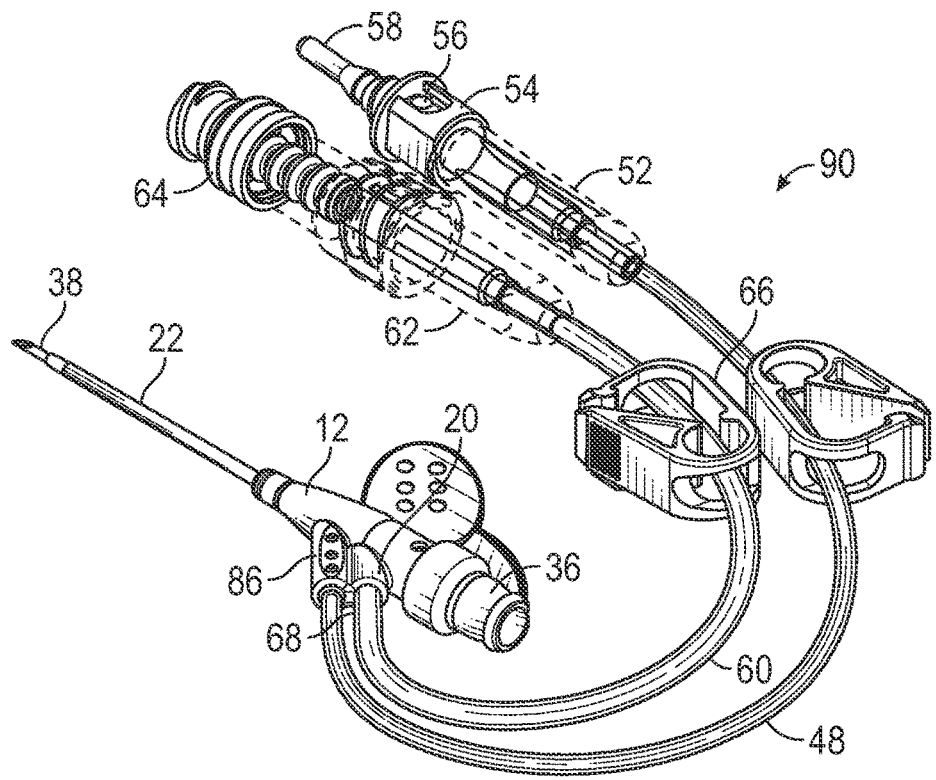
FIG. 4C is an upper perspective view of another catheter system, according to some embodiments.
Figure 4D:
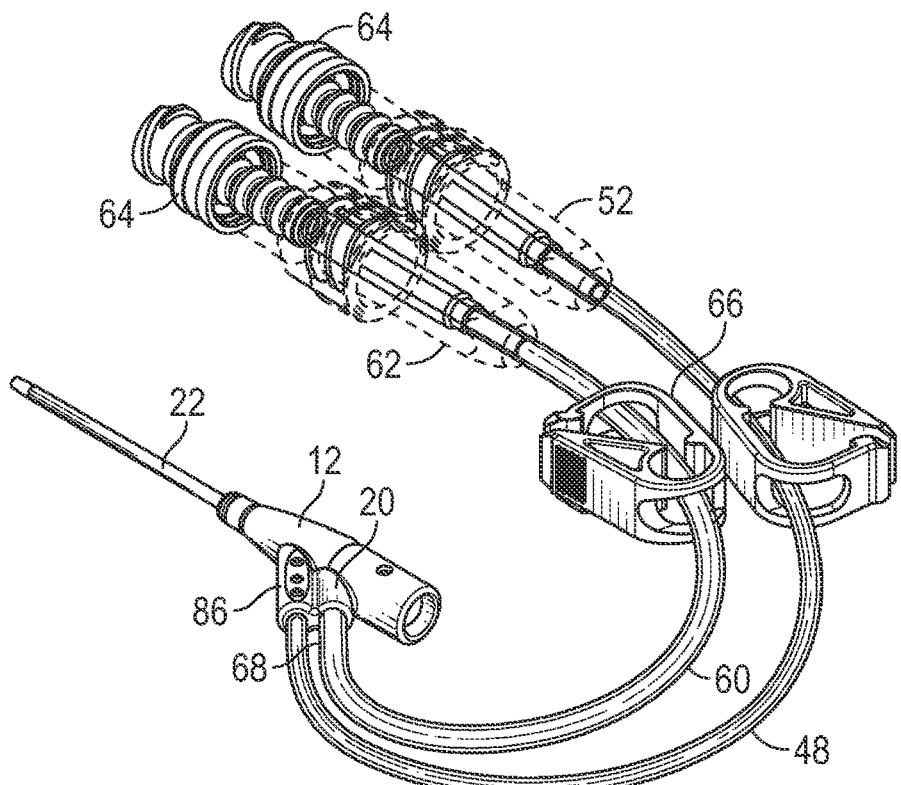
FIG. 4D is an upper perspective view of the catheter system of FIG. 4C, illustrating an example plug replaced with an example needleless connector, according to some embodiments.

Referring now to FIGS. 4C-4D, another catheter system 90 is illustrated, according to some embodiments. In some embodiments, the catheter system 90 may be similar or identical in terms of one or more included components and/or operation to the catheter system 10 described with respect to FIGS. 1-3 and/or the catheter system 85 described with respect to FIG. 4. In some embodiments, a distal end of the extension tube 48 may be integrated with the other side port 86. In FIG. 4D, the plug 54 is replaced with a needleless connector 64 after blood is drawn from the vasculature of the patient, which may facilitate flushing. In some embodiments, one or more of the needleless connectors 64 may be used to flush the catheter system 90. In some embodiments, the dual-extension tube configuration of the catheter system 90 may facilitate immediate blood collection upon catheter insertion into the vasculature and parallel drug delivery. In some embodiments, at any point during an indwell period of the catheter system 90, blood draw may be initiated by replacing one of the needleless connectors 64 with a plug 54.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

I claim:

1. A catheter system, comprising: a catheter adapter, comprising a distal end, a proximal end, a lumen extending through the distal end and the proximal end, and a side port in fluid communication with the lumen, wherein the catheter adapter further comprises a slot extending from the proximal end of the catheter adapter; a catheter extending distally from the catheter adapter; a septum disposed within the lumen of the catheter adapter, wherein the septum comprises a first slit and a second slit generally parallel to the first slit, wherein the first slit is generally aligned with a longitudinal axis of the catheter, wherein the second slit is offset from the longitudinal axis of the catheter, wherein the slot is laterally offset from the longitudinal axis of the catheter towards the side port; a needle hub; and an introducer needle secured within the needle hub, wherein the introducer needle is aligned with the longitudinal axis of the catheter and extends through the catheter and the first slit of the septum, wherein the slot is parallel to the introducer needle.

2. The catheter system of claim 1, wherein the septum comprises a generally elliptical shape with a cut along a plane angled with respect to the longitudinal axis of the catheter.

3. The catheter system of claim 2, wherein the cut forms a first face at a distal end of the septum, wherein the distal end of the septum comprises the first face and a second face, wherein the second face is proximate the first face and generally perpendicular to the longitudinal axis of the catheter.

4. The catheter system of claim 3, wherein the septum comprises a tunnel extending along the first face, wherein the tunnel extends from the side port towards the longitudinal axis of the catheter.

5. The catheter system of claim 1, further comprising a winged needle set, comprising:
a body;
a tab extending outwardly from the body, wherein the tab is disposed within the slot;
a needle extending distally from the body and through the second slit of the septum;
an extension tube extending from the body.

6. The catheter system of claim 5, wherein the winged needle set further comprises:
- an adapter coupled to a proximal end of the extension tube; and
- a plug plugging a proximal end of the adapter, wherein a proximal end of the plug is configured to couple to a blood collection device, wherein the plug provides air venting of the winged needle set.

7. The catheter system of claim 5, wherein a distal end of the needle is blunt.

8. The catheter system of claim 5, wherein a distal end of the needle is sharp.

9. The catheter system of claim 1, wherein the proximal end of the catheter adapter comprises a proximal opening, wherein the longitudinal axis of the catheter is offset from a center of the proximal opening.

10. A catheter system, comprising: a catheter adapter, comprising a distal end, a proximal end, a lumen extending through the distal end and the proximal end, and a side port in fluid communication with the lumen; a catheter extending distally from the catheter adapter; a septum disposed within the lumen of the catheter adapter, wherein the septum comprises a first slit and a second slit generally parallel to the first slit, wherein the first slit is generally aligned with a longitudinal axis of the catheter, wherein the second slit is offset from the longitudinal axis of the catheter; a needle hub; and an introducer needle secured within the needle hub, wherein the introducer needle is aligned with the longitudinal axis of the catheter and extends through the catheter and the first slit of the septum, wherein a cut forms a first face at a distal end of the septum, wherein the distal end of the septum comprises the first face and a second face, wherein the second face is proximate the first face and generally perpendicular to the longitudinal axis of the catheter, wherein the septum comprises a tunnel extending along the first face, wherein the tunnel extends from the side port towards the longitudinal axis of the catheter.

11. The catheter system of claim 10, wherein the catheter adapter further comprises a slot extending from the proximal end of the catheter adapter, further comprising a winged needle set, comprising:
- a body;
- a tab extending outwardly from the body, wherein the tab is disposed within the slot;
- a needle extending distally from the body and through the second slit of the septum; and
- an extension tube extending from the body.

12. The catheter system of claim 11, wherein the winged needle set further comprises:
- an adapter coupled to a proximal end of the extension tube; and
- a plug plugging a proximal end of the adapter, wherein a proximal end of the plug is configured to couple to a blood collection device, wherein the plug provides air venting of the winged needle set.

13. A catheter system, comprising: a catheter adapter, comprising a distal end, a proximal end, a lumen extending through the distal end and the proximal end, and a side port in fluid communication with the lumen, wherein the catheter adapter further comprises a slot extending from the proximal end of the catheter adapter; a catheter extending distally from the catheter adapter; a septum disposed within the lumen of the catheter adapter, wherein the septum comprises a first slit and a second slit generally parallel to the first slit, wherein the first slit is generally aligned with a longitudinal axis of the catheter, wherein the second slit is offset from the longitudinal axis of the catheter, wherein the slot is laterally offset from the longitudinal axis of the catheter towards the side port; a needle hub; an introducer needle secured within the needle hub, wherein the introducer needle is aligned with the longitudinal axis of the catheter and extends through the catheter and the first slit of the septum; and a winged needle set comprising a tab disposed in the slot and a needle extending through the second slit of the septum, wherein the needle intersects a central axis of the side port and is configured to receive blood flashback therethrough.

14. The catheter system of claim 13, wherein the septum comprises a generally elliptical shape with a cut along a plane angled with respect to the longitudinal axis of the catheter.

15. The catheter system of claim 14, wherein the cut forms a first face at a distal end of the septum, wherein the distal end of the septum comprises the first face and a second face, wherein the second face is proximate the first face and generally perpendicular to the longitudinal axis of the catheter.

16. The catheter system of claim 15, wherein the septum comprises a tunnel extending along the first face, wherein the tunnel extends from the side port towards the longitudinal axis of the catheter.

* * * * *